United States Patent [19]
Curry

[11] Patent Number: 6,152,938
[45] Date of Patent: Nov. 28, 2000

[54] DEVICE FOR OPENING BLOCKED TUBES

[76] Inventor: Paul Curry, London Bridge Hospital, Emblem House, London Bridge, 27 Tooley Street, London SE1 2PR, United Kingdom

[21] Appl. No.: 09/136,717

[22] Filed: Aug. 19, 1998

[30] Foreign Application Priority Data

Aug. 19, 1997 [GB] United Kingdom ............... 9717580

[51] Int. Cl.⁷ ............................................. A61B 17/32
[52] U.S. Cl. ............................................................ 606/159
[58] Field of Search ................................. 606/159, 170, 606/180; 600/470, 467; 604/22

[56] References Cited

U.S. PATENT DOCUMENTS

| | | | |
|---|---|---|---|
| 4,898,575 | 2/1990 | Fischell et al. | 606/159 |
| 4,935,025 | 6/1990 | Bundy et al. | 606/180 |
| 5,047,040 | 9/1991 | Simpson et al. | 606/159 |
| 5,078,723 | 1/1992 | Dance et al. | 606/159 |
| 5,306,244 | 4/1994 | Shiber | 606/159 |
| 5,314,438 | 5/1994 | Shturman | 606/159 |
| 5,507,292 | 4/1996 | Jang et al. | 128/660.03 |
| 5,649,941 | 7/1997 | Lary | 606/170 |

FOREIGN PATENT DOCUMENTS

| | | |
|---|---|---|
| 0254414 | 1/1988 | European Pat. Off. . |
| 0360791 | 9/1989 | European Pat. Off. . |
| 0448859 | 10/1991 | European Pat. Off. . |
| 0657140 | 6/1995 | European Pat. Off. . |
| 9313716 | 7/1993 | WIPO . |

*Primary Examiner*—Michael Buiz
*Assistant Examiner*—Kevin Troung
*Attorney, Agent, or Firm*—Hodgson, Russ, Andrews, Woods & Goodyear LLP

[57] ABSTRACT

A drill member comprising a drill head located at the distal end of a catheter. The drill further includes a divice for anchoring the tip of the drill head against at least a portion of a face of occulusion whilst allowing the drill to rotate.

14 Claims, 14 Drawing Sheets

DEVICE FOR OPENING BLOCKED TUBES

BACKGROUND OF THE INVENTION

The present invention relates to a device for opening blocked tubes. More particularly the present invention relates to a device for opening blocked tubes in the human or animal body, particularly blocked blood vessels. For ease of reference, various tubes that may be found in the human or animal body will be referred to as "biological tubes".

Tubes may become blocked for a variety of reasons and the consequences of the blockages vary depending on the nature of the tube and the location of the blockage. Even partial blocking of tubes may cause difficulties such as reducing the rate of flow of any fluid flowing in the tube. Where the tube is a biological tube, partial blocking may result in the patient suffering from mild to severe pain depending on the extent of the blockage. The problem may be particularly severe where the partial blockage occurs in an artery such as a coronary artery.

Present techniques enable such partially blocked tubes to be opened by means of a technique known as hydraulic stretch. This technique, which is particularly common in the field of biological tubes and more particularly blood vessels requires that a guide wire is inserted into the vessel such that it extends through the narrowed region of the tube. A deflated balloon, located at the distal end of a catheter, is then passed along the guide wire to the narrowed segment. This may be via an over-the-wire technique where the catheter actually surrounds the wire or via an arrangement known as the mono-rail technique whereby the catheter is suspended from the wire.

Once the balloon is in place in the narrowing it is inflated and the narrowed artery is thereby stretched such that the pathway in the centre of the tube is fully opened. This technique is very effective and, in the case of biological tubes, as it is minimally invasive, often being performed under local anaesthetic through a percutaneous puncture from a remote site, is of minimal distress to the patient.

The same technique may be utilised where the occlusion is total, ie where the tube is substantially completely blocked, provided that the material forming the occlusion is sufficiently soft to enable the guide wire and the catheter to be pushed through the blocking mass.

However, if the occlusion is hard such as where it has been formed for some time, it may not be possible to push a guide wire through the blocking mass and thus a balloon catheter of the type described above cannot be used. It is therefore necessary for an alternative arrangement to be made for overcoming the effects of the blockage. Where the tube is a biological tube the patient generally will have to undergo major surgery such that the occlusion may be bypassed. Such operations are traumatic for the patient and it is therefore desirable that means be provided that enable total occlusions to be opened without the need for surgery, ie. that can be carried out with minimal trauma to the patient, such as through a percutaneous puncture under local anaesthetic.

SUMMARY OF THE INVENTION

It has now been discovered that the above object can be achieved by the provision of a drill which is inserted into the blocked tube to drill through the occlusion to thereby open the occlusion. The opening may be total, ie all of the blocking mass may be removed, or sufficient such that conventional opening techniques, such as that involving the use of the balloon catheter described above, may be employed. In general, where the tube walls are formed from delicate material, such as in biological tubes, the drill will generally be operated such that it does not abraid the walls of the tubes.

According to the present invention there is provided a drill means comprising a drill head located at the distal end of a catheter and means for anchoring the tip of the drill head against at least a portion of the face of an occlusion whilst allowing the drill to rotate.

The catheter supporting the drill head will in general be flexible to enable it to travel from an entry point to the location of the occlusion. As tubes in general, and in particular, biological tubes, such as blood vessels, are not straight, a flexible catheter will be required to enable it to pass through tubes to the site of the occlusion. Where the occlusion is in the heart, the entry point of the device into the patient's body would normally be in the leg. However, in some applications the blocked tube may be substantially straight in which case a rigid catheter may be used.

The anchoring means is required to hold the head of the drill against the face of the occlusion and thereby prevent it from moving away from the occlusion and possible damaging the wall of the tube during drilling. This is particularly important where the catheter is flexible or the walls of the tube are weak.

The anchoring means is preferably of longitudinal configuration and is located centrally along the axis of the catheter and extends along the length thereof. The anchoring means therefore may also act as a guide wire for the catheter and its integral drill head and thereby assist in the insertion of the device into the tube to the site of the occlusion.

The anchoring device is preferably retractable into the drill head such that a smooth forward surface is presented. This is particularly advantageous where the drill device is to be inserted into the body and will minimise any risk of damage to the walls of the tube into which the device is inserted.

Once the device has been inserted into the tube such that the drill head abuts the face of the occlusion, the anchoring device is advanced into the occlusion. Normally, in the case of occlusions in biological tubes, the advance will be a short advance of the order of 1 to 3 mm, preferably 2 mm. However, the length of the advancement will be selected depending on the tube and the material from which the occlusion is formed. The advancement of the anchoring means may be accomplished by any suitable means. For example, it may be driven into the occlusion by pressure or in one particularly preferred embodiment it may itself be drilled into the occlusion.

Thus, the anchoring device preferably comprises a line which is attachable at a proximal end to a machine which, when operated, will cause the line to rotate and which has, at its distal end, a drill tip. The drill tip may be fabricated from any suitable material and may be of any suitable configuration. The configuration and material selected may be selected such that it is appropriate for insertion into the occlusion and thus will depend on the nature of the material from which the occlusion is formed. The diameter of the drill tip will depend on the tube into which the device is to be inserted, however, for a coronary artery the drill tip of the anchoring device will commonly have a diameter of approximately 0.014" to 0.035".

Once the anchoring device has been advanced into the occlusion to a sufficient depth, the drill head will be caused to rotate by any suitable means such that it is drilled into the occlusion. It will be advanced until it reaches the forward end of the anchoring device. Drilling will then be ceased and the process of advancing the anchoring device will be repeated.

In general, it will be desirable that the operator of the device has an image of the location of the drill head in the tube. This will be particularly important where the tube is a biological tube and care must be taken to ensure that the drill does not come into contact with the wall of the tube.

The visualisation of the location of the drill may be achieved by any suitable means. The visualisation may be achieved from outside the tube or where the tube is buried inside a body, for example a biological tube or a tube forming part of domestic or industrial plumbing which is located inside a larger piece of apparatus. Suitable visualisation means include X-rays and infra-red sensors.

Alternatively, the visualisation may be achieved by means of a signal emitted from the device itself. Suitable means include ultrasound.

The visualisation may be used to enable the operator to know the location of the device within the length of the tube. Additionally, or alternatively, it may be used to enable the user to visualise whether the drill is located co-axially in the tube, ie that it is located centrally within the tube. Thus, the visualisation may view the walls of the tube.

It is known to be use ultrasound in medical techniques such as opening biological tubes utilising the balloon catheters. In these arrangements a probe is inserted into the tube and ultrasound waves are emitted and subsequently detected by conventional means to build up a picture of the walls of the tube. The ultrasound waves are emitted radially from the probe and thus, the picture that is built up is one of the walls directly surrounding the probe.

In the present invention, whilst it would be useful to have information relating to the configuration of the walls of the tube surrounding the drill it would be particularly advantageous to be able to image the configuration of the tube ahead of the distal end of the drill means such that the user can confirm that the drill is being applied centrally in the occluded tube. Thus, according to a preferred aspect of the present invention, the device includes imaging means. The imaging means preferably comprise ultrasound means. In a particularly preferred arrangement the ultrasound means comprises a phased array ultrasound device. In one arrangement the array of ultrasound emitters are located on the surface of the drill head. In another arrangement they are recessed into the drill head and may be covered by an ultrasound transparent cover to prevent damage to the emitters being caused by friction with the blocking mass. In one alternative arrangement the ultrasound may be a single emitter and the drill head may be caused to spin during the imaging step to enable a suitable picture to be obtained.

In an alternative arrangement, there may be located behind the drill head, a collar surrounding the external wall of the device. A further array of ultra sound emitters may be located in the collar and connected to the imaging means. This further array of ultrasound emitters would then provide an accurate guide as to the position of the body of the device with respect to the side walls of tube.

Where the tube has curves, or bends, means will be required that enable the user to turn the drill head such that the drilling path remains substantially central of the axis of the tube. In order to increase the ease with which the head can turn in a channel which will have substantially the same diameter as the diameter of the drill head, the forward face the drill head will preferably be of a hemispherical configuration. Means may be provided to enable the user to turn the drill head within the tube. Any suitable means may be used including remote control means.

In a particularly preferred arrangement reins may be provided extending from the rear of the drill head which will enable the user to steer the head by increasing the tension on one or more rein. Where the tube may bend in any direction, the drill head will normally be provided with four reins to enable the head to be steered upwardly, downwardly, leftwardly or rightwardly. The application of tension to two or more reins enables the user to adjust the drill head accurately.

The reins may be fabricated from any suitable material. Particularly preferred materials would include stainless steel wire and polymeric plastics material. The materials are preferred as they are flexible enough to bend around corners whilst being sufficiently rigid to bend the device when the reins are "pushed" in addition to bending the device in the opposite direction when the reins are "pulled".

In this arrangement the reins must be free to move along the length of the catheter. Therefore, the catheter may have conduits or other types of microtubes that run the full length of the catheter, in which the reins may be positioned. Alternatively, means may be provided on the outside of the catheter to allow this movement of the reins. Such means may include a large number of loops embedded perpendicularly into the outside wall of the catheter and through which the reins are passed, although any suitable means may be used.

In a further arrangement, at least one collar may be placed around the outside of the tube to provide a leverage means against which the reins may act to enable the catheter to bend. In the arrangement incorporating a collar and ultrasound emitter array behind the drill head, this collar may also function as the leverage means.

As the drilling will cause debris to be formed, the device preferably includes a vacuum line extending along the catheter internally or externally. The mouth of the vacuum line may extend to the face of the drill head or may be located behind the drill head. The vacuum line will be attached to a suitable vacuum means.

The device may also include a means for inserting a flushing liquid to the drilling site. This liquid may be used to assist in the removal of debris. In some circumstances, depending on the material from which the occlusion is formed, the liquid may be required to cool the drill head. Again, the line for supplying the flushing liquid will generally extend along the catheter internally or externally and may open at the face of the drill head or behind the drill head. Any suitable flushing liquid may be utilised. Where the tube is a biological tube, saline will normally be used.

At a site remote from the patient, the user will have suitable controls to enable him to individually power the anchoring means and the drill head, together with, where appropriate, means for converting signals to aid in the visualisation of the drilling site. The controls of the anchoring means, the drill head, the visualisation and any flushing or vacuum lines may be provided at a single site via means such as a mouse or joy stick. The power for the anchoring means and drill head may be provided from a single switchable source.

Whilst occlusions in tubes may occur in both biological tubes and non-biological tubes, the present invention will be described in detail, by way of example, with specific reference to a total occlusion located in a coronary artery.

The present invention will now be described, by way of example, with reference to the accompanying drawings in which:

Brief Description of the Drawings

| | |
|---|---|
| FIG. 1 | is a schematic diagram of the coronary arteries; |
| FIG. 2 | is a cross-sectional view of the present invention with the anchoring means advanced, (the anchoring means shown in perspective view); |
| FIG. 3 | is a perspective view of the anchoring means; |
| FIG. 4 | is a schematic representation of the device located against an occlusion in a tube, anchoring means retracted; |
| FIG. 5 | is a schematic representation of the device located against an occlusion in a tube, anchoring means advanced into the occlusion; |
| FIG. 6 | is a schematic representation of the device wherein the drill head has advanced into the occlusion; |
| FIG. 7 | is a schematic representation of the device wherein the drill head has advanced into the occlusion to a bend in the tube; |
| FIG. 8 | is a schematic representation of the device wherein the drill head has been turned with the bend by applying pressure to the reins; |
| FIG. 9 | is a schematic representation of the face of the drill head; |
| FIG. 10 | is a schematic representation of the drill head with one rein in place; |
| FIG. 11 | is a schematic represnetation of the face of the drill head with the ultrasound array illustrated; |
| FIG. 12 | is a cross-sectional view of the shaft with two ultrasound emitters depicted (anchoring means removed); |
| FIG. 13 | is a cross-sectional view of the detail of the shaft of the device looking towards the drill head; and |
| FIG. 14 | is a cross-sectional view of the detail of one arrangement of the shaft (anchoring means removed). |

DETAILED DESCRIPTION OF THE INVENTION

Figure 1:
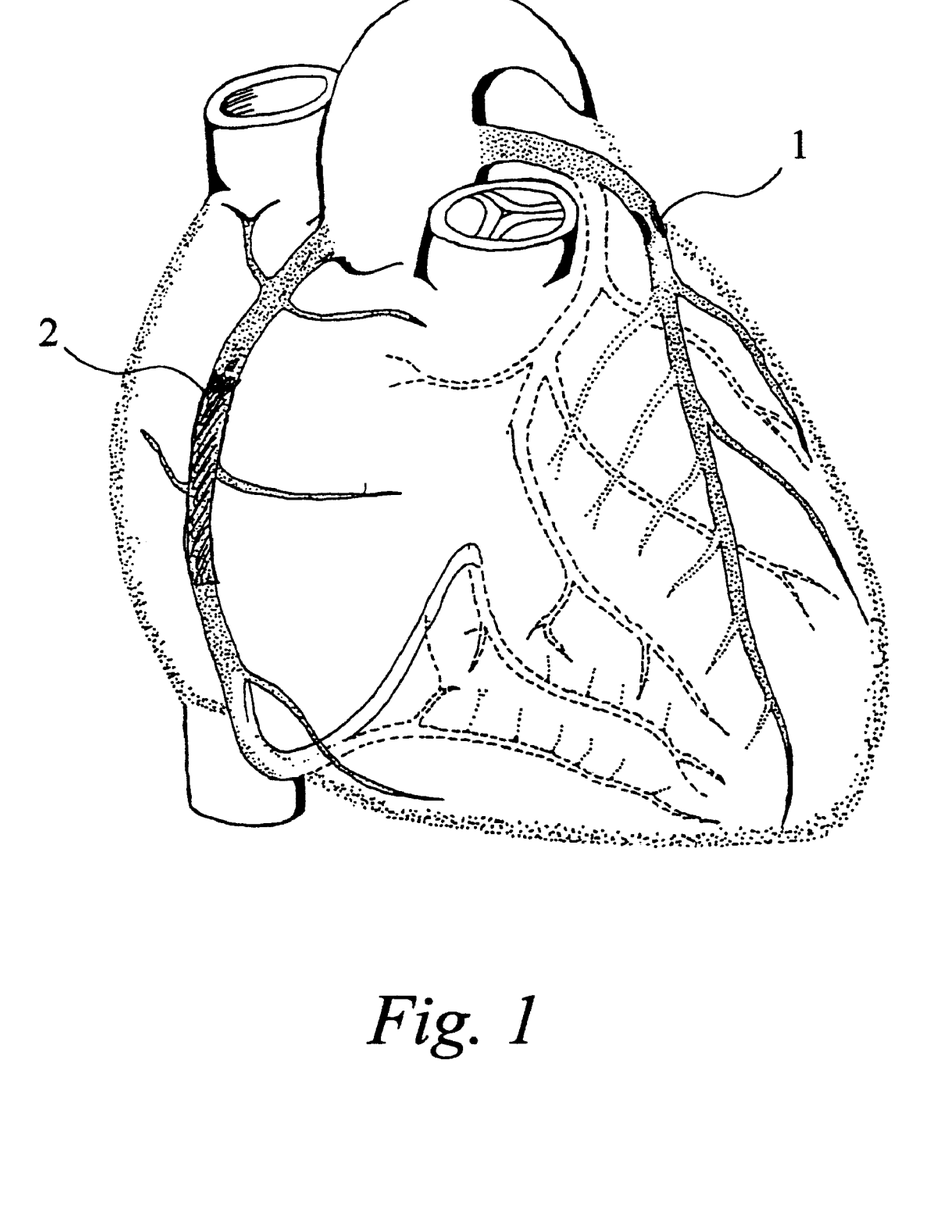

As illustrated in FIG. 1 occlusions may occur in coronary arteries. A partial occlusion 1 which may be treated with the balloon catheters of the prior art may form. A total occlusion 2 may also be formed which normally requires major surgery to bypass the occlusion.

Figure 2:
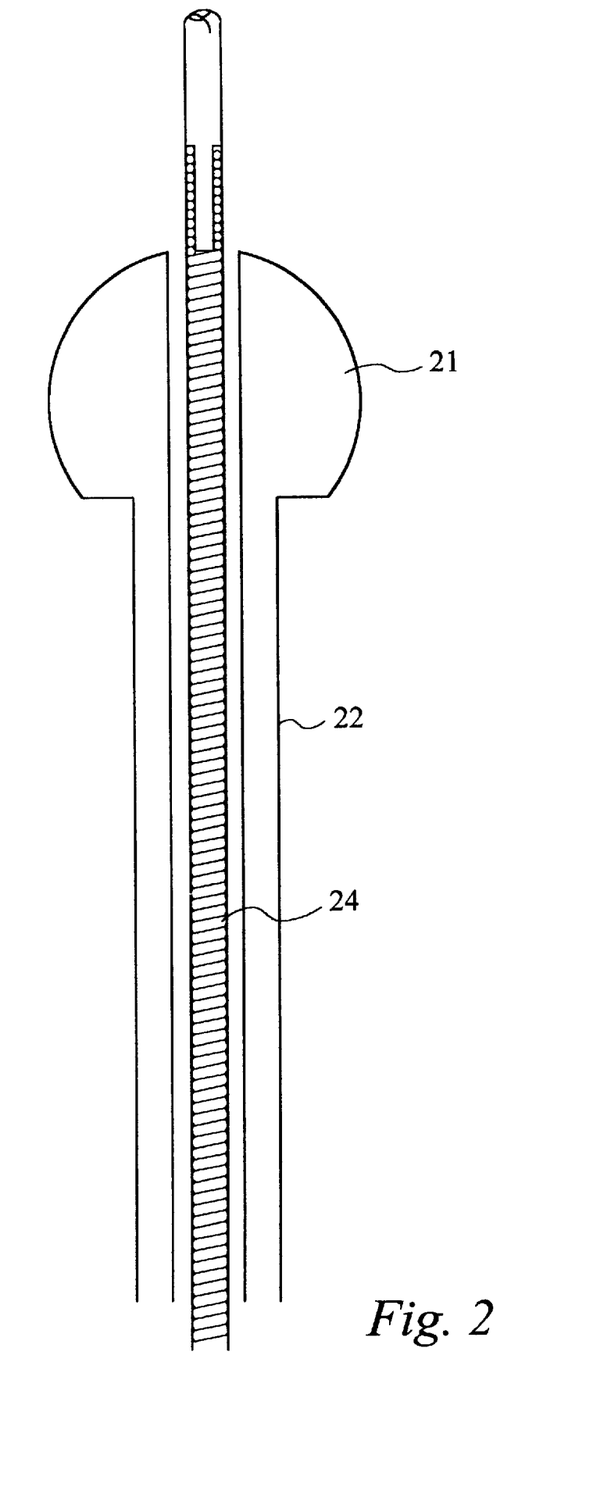
Figure 3:
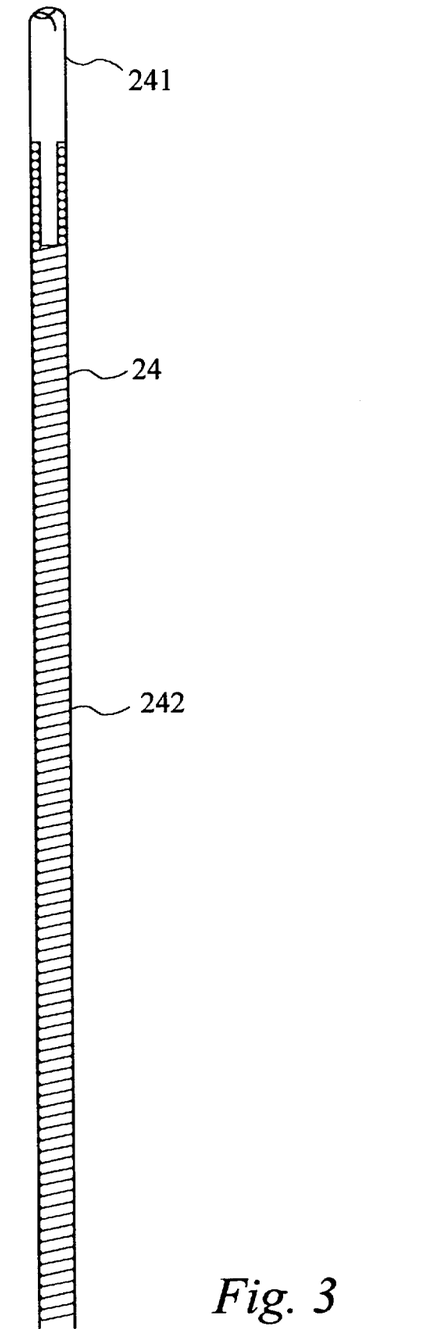

As illustrated in FIG. 2 the device of the present invention comprises a drill head 21 connected by suitable means to a flexible catheter 22. The flexible catheter may be formed from any suitable material. Particularly suitable material is a polyethylene. The end of the catheter remote from the drill head will be held in a chuck (not shown) such that it can be caused to rotate to activate the drill. The drill head 21 may be of any suitable configuration but will preferably have a hemispherical face to enable it to be turned within a confined space. The anchoring means 24 is shown in detail in FIG. 3. The anchoring means comprises a drill tip 241 and a flexible support wire 242. The drill tip may be of any configuration but will generally be the configuration of a conventional drill bit. The tip will be connected by a suitable means to the flexible drill wire 242 which may be formed from any suitable material, including plastics. However, a metallic wire will be preferred. The end of the wire remote from the tip will be held in a chuck (now shown) such that it can be caused to rotate.

Figure 4:
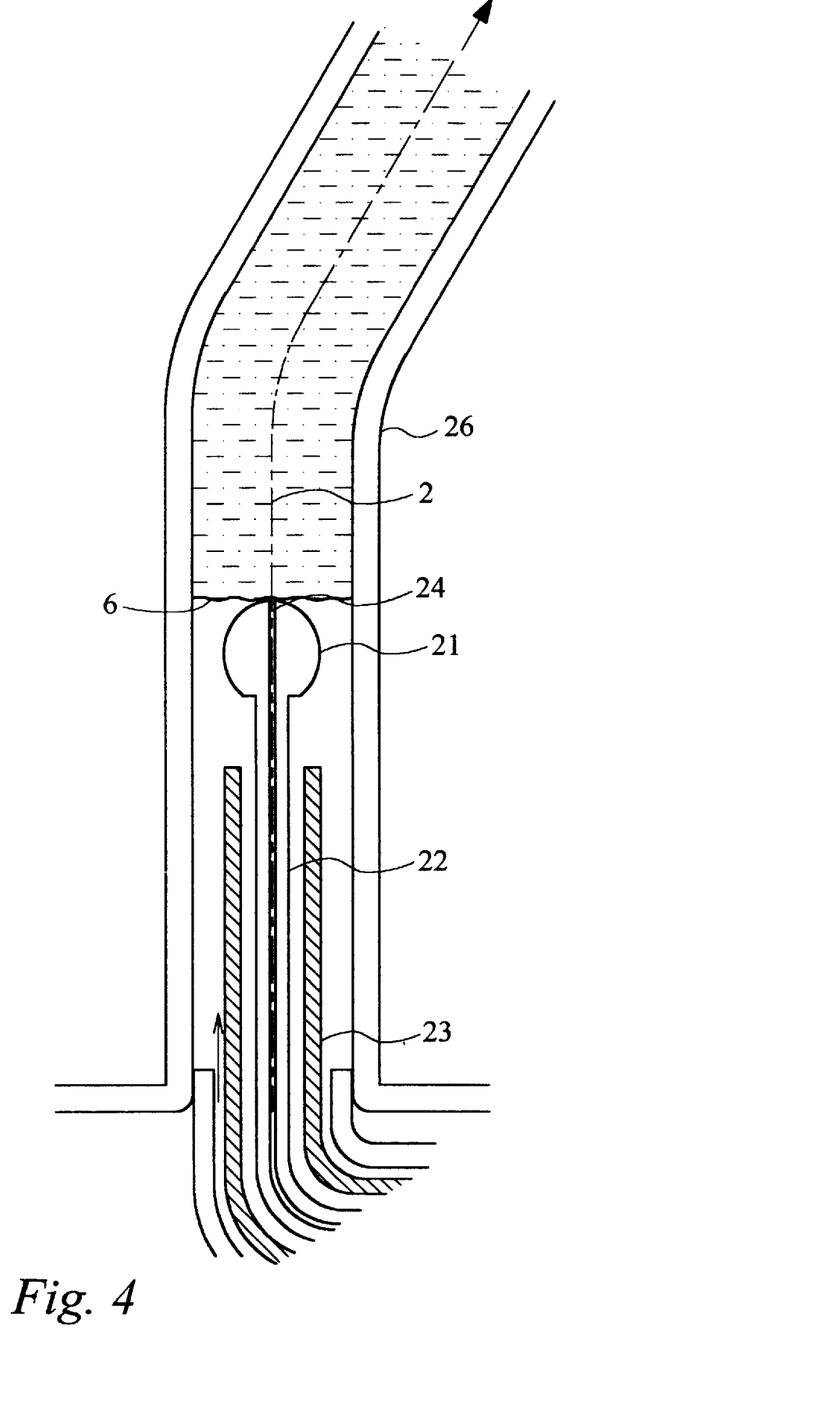

In order to treat a total occlusion 2 the device of the present invention is inserted into the body and using conventional techniques is advanced until it abuts the face 6 of the occlusion 2 as shown in FIG. 4. The device will be located such that it is centrally within the walls of the tube 26. As shown in FIG. 4 the flexible catheter 22 may itself be housed in a sheath 23. At the point at which the device of the present invention abuts the occlusion, the anchoring means 24 will be recessed within the drill head 21.

Figure 5:
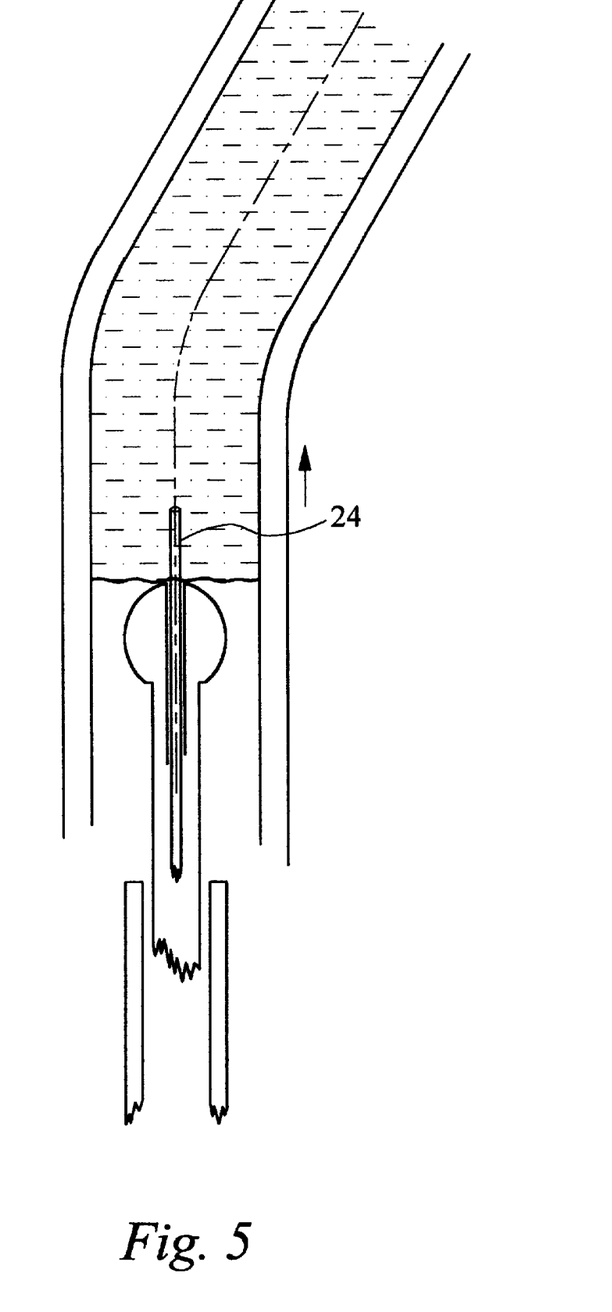
Figure 6:
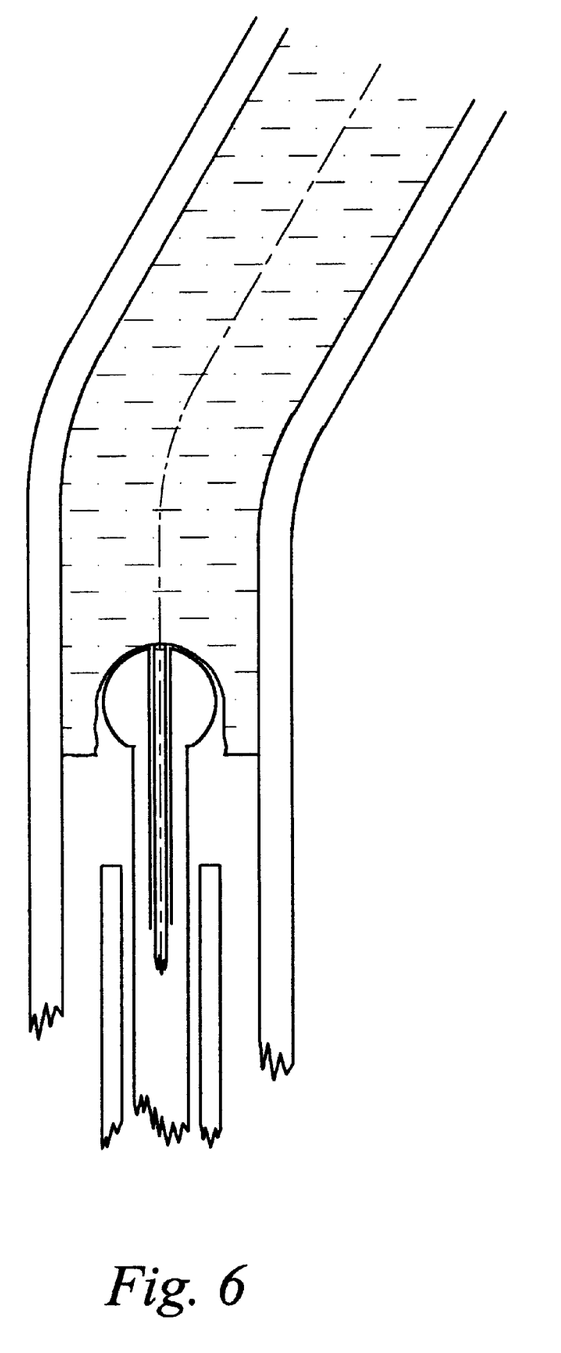

The anchoring means will then be activated such that the drill tip is advanced into the occlusion by a suitable distance as shown in FIG. 5. The rotation of the drill wire will then be ceased and the user will cause the catheter and the drill head connected thereto to rotate and move forwardly such that the drill head moves into the occlusion. As shown in FIG. 6 the advancement of the drill head into the occlusion will generally be to the position such that the anchoring means is again located within the drill head. That is to say that it has been extended forwardly as far as the anchoring means was initially advanced. The process may then be repeated. In some arrangements, the drill head may extend forwardly to a position advanced of the position to which the anchoring means was extended.

Depending on the nature of the material from which the occlusion is formed, it may not be necessary to use the anchoring means once the drill head is located within the self-formed channel and provided that the tube is straight.

Figure 7:
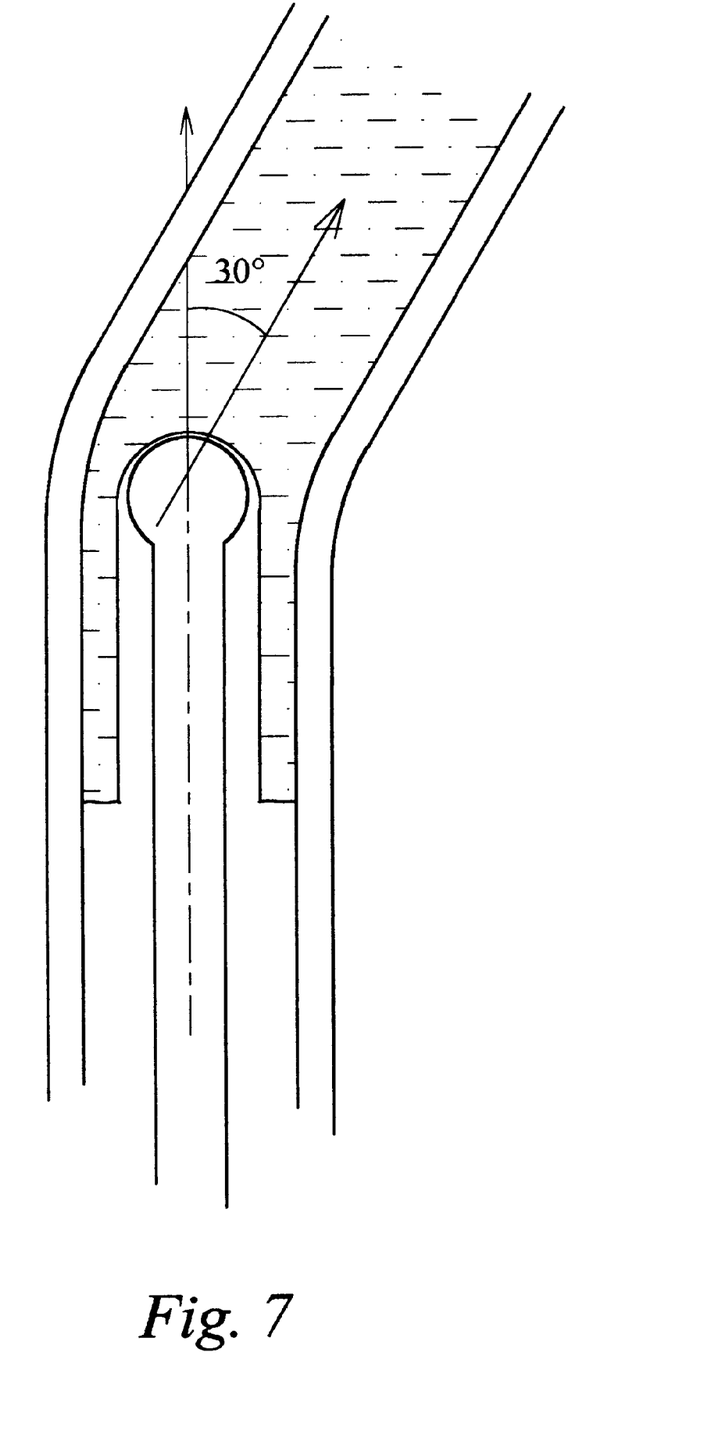

As illustrated in FIG. 7, where a bend or curve is located in the tube, if the drill head were to proceed in a forwardly direction, it would pass through the wall of the tube. It is therefore necessary to turn the drill such that drilling proceeds along the new direction of the tube.

Figure 8:
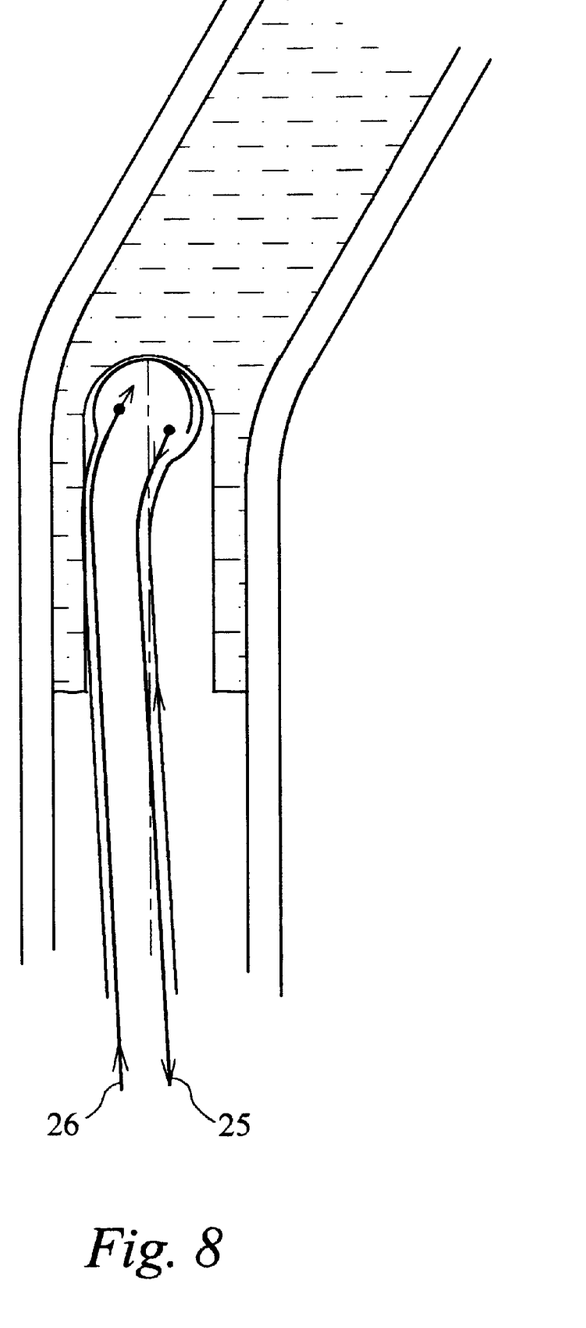

The device would generally be provided with four reins (two illustrated, 25 & 26) spaced around drill head 21 to enable the user to control the orientation of the head. At the site of the bend, as visualised using the ultrasound technique, one or more reins 26 will be tensioned to enable the head to be turned to face along the axis of the tube. The flexible nature of the catheter 22 enables it to move within the channel and thereby assist the alteration of the drilling direction. The anchoring means will then be activated to pin the head in its new orientation. Once the head has been anchored, the tension applied to the reins will be released and the drill head advanced in the normal manner.

Figure 9:
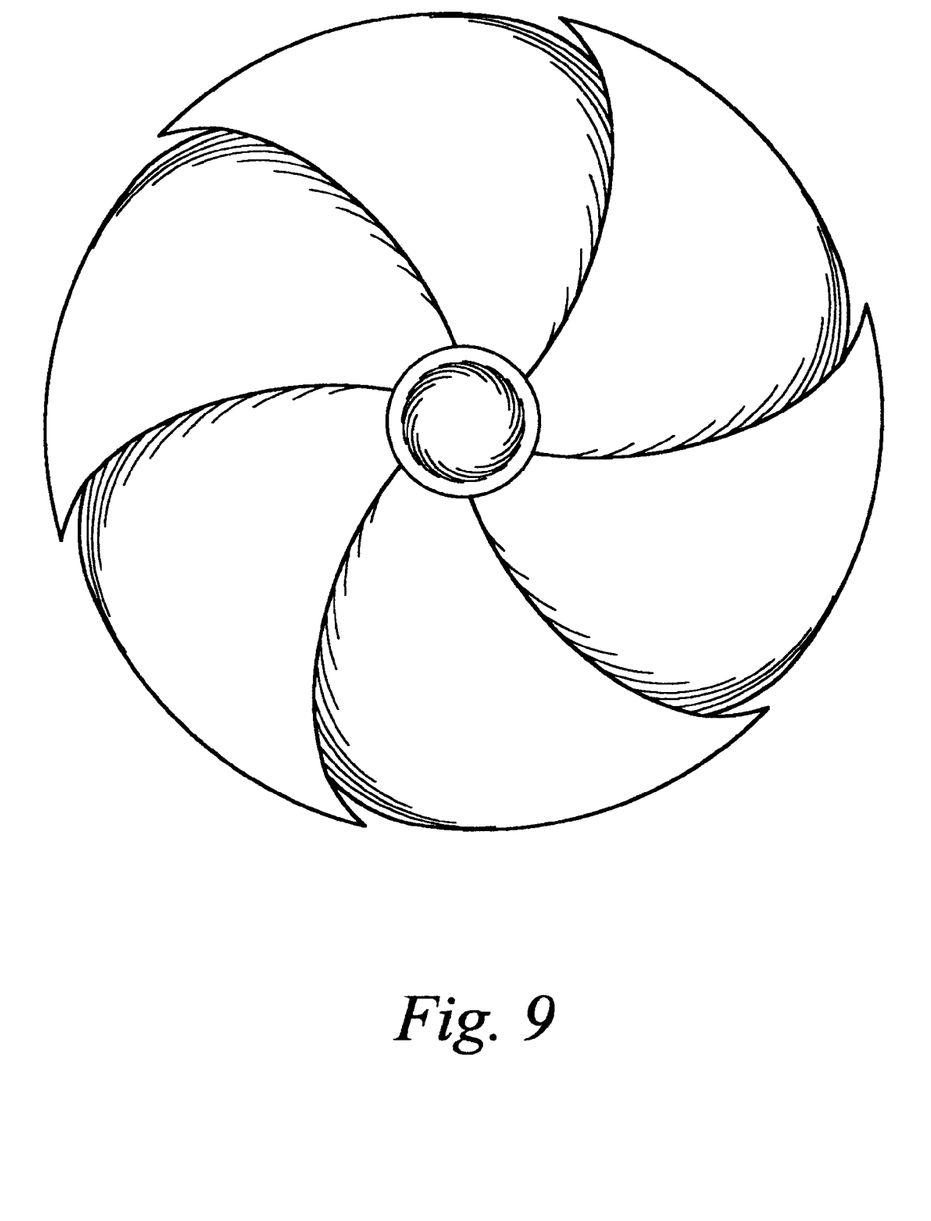

FIG. 9 illustrates one suitable arrangement for the surface of the drill head. It will be understood that nay suitable configuration will be utilised and that the drill head may not have teeth of the kind illustrated but may be a single surface that is abrasive. For example, the drill head may be diamond tipped, such as a diamond burr type drill head or may be formed of any other suitably abrasive material.

Figure 10:
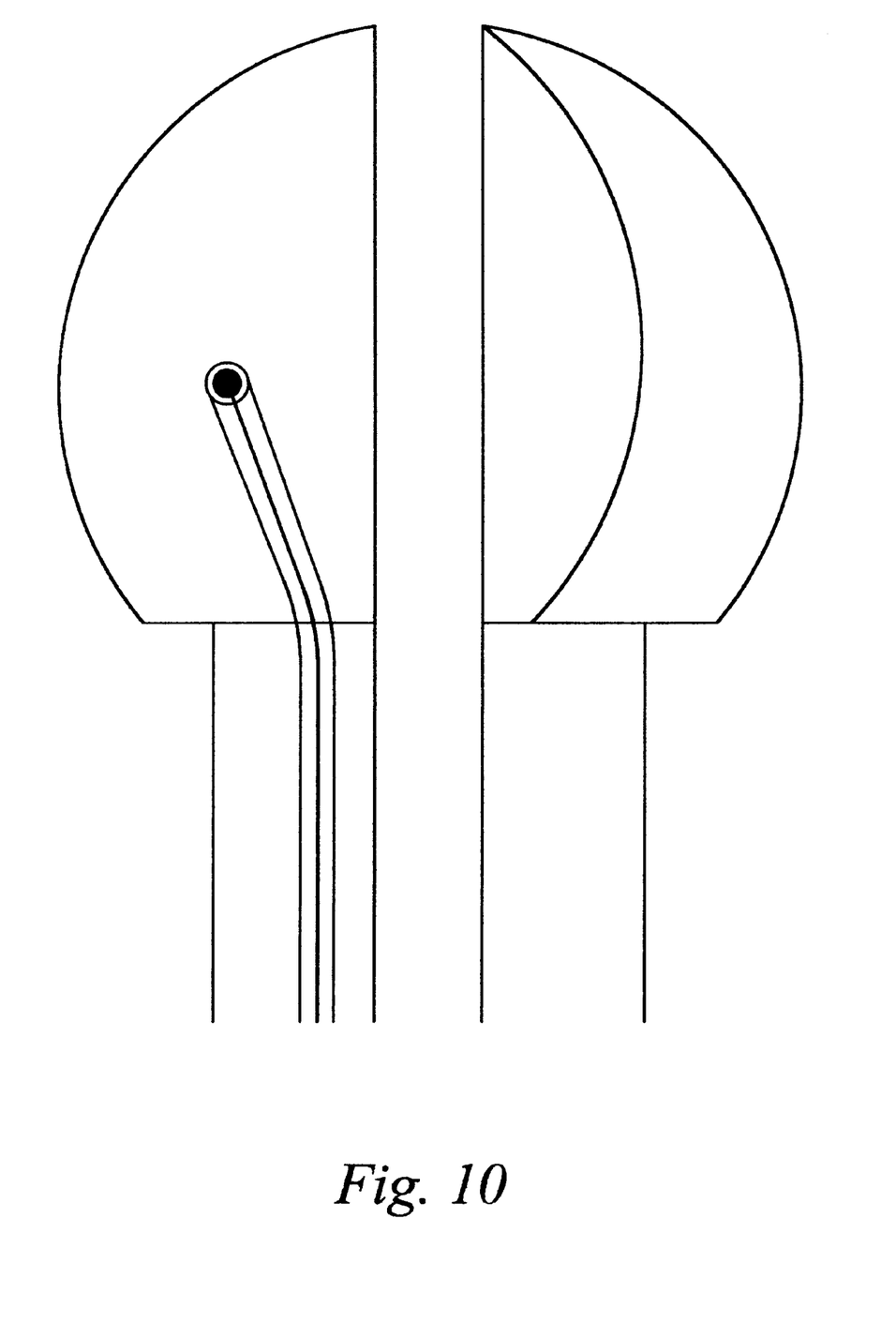

FIG. 10 illustrates one means of locating a rein within the drill head. The rein may be buried in the head as shown with reins extending in channels along the catheter or, in one alternative, the rein may be attached to the base of the head.

Figure 11:
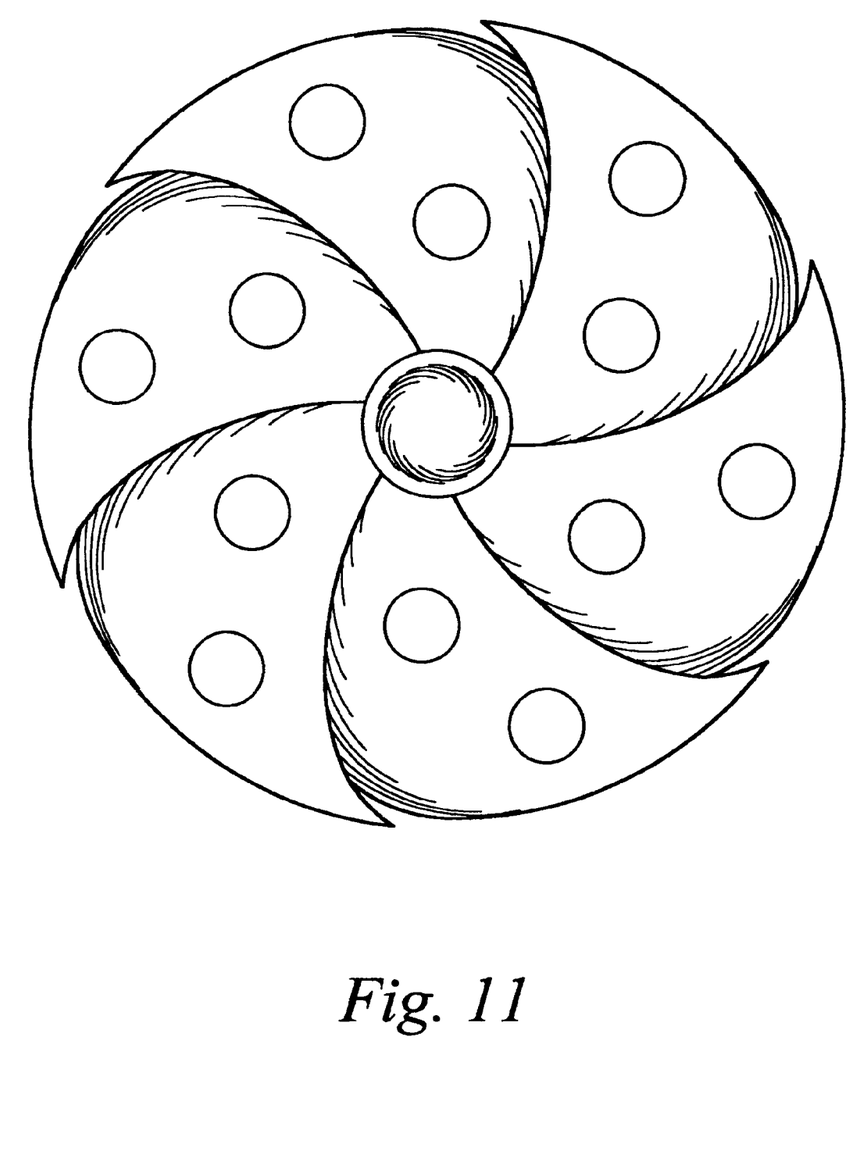
Figure 12:
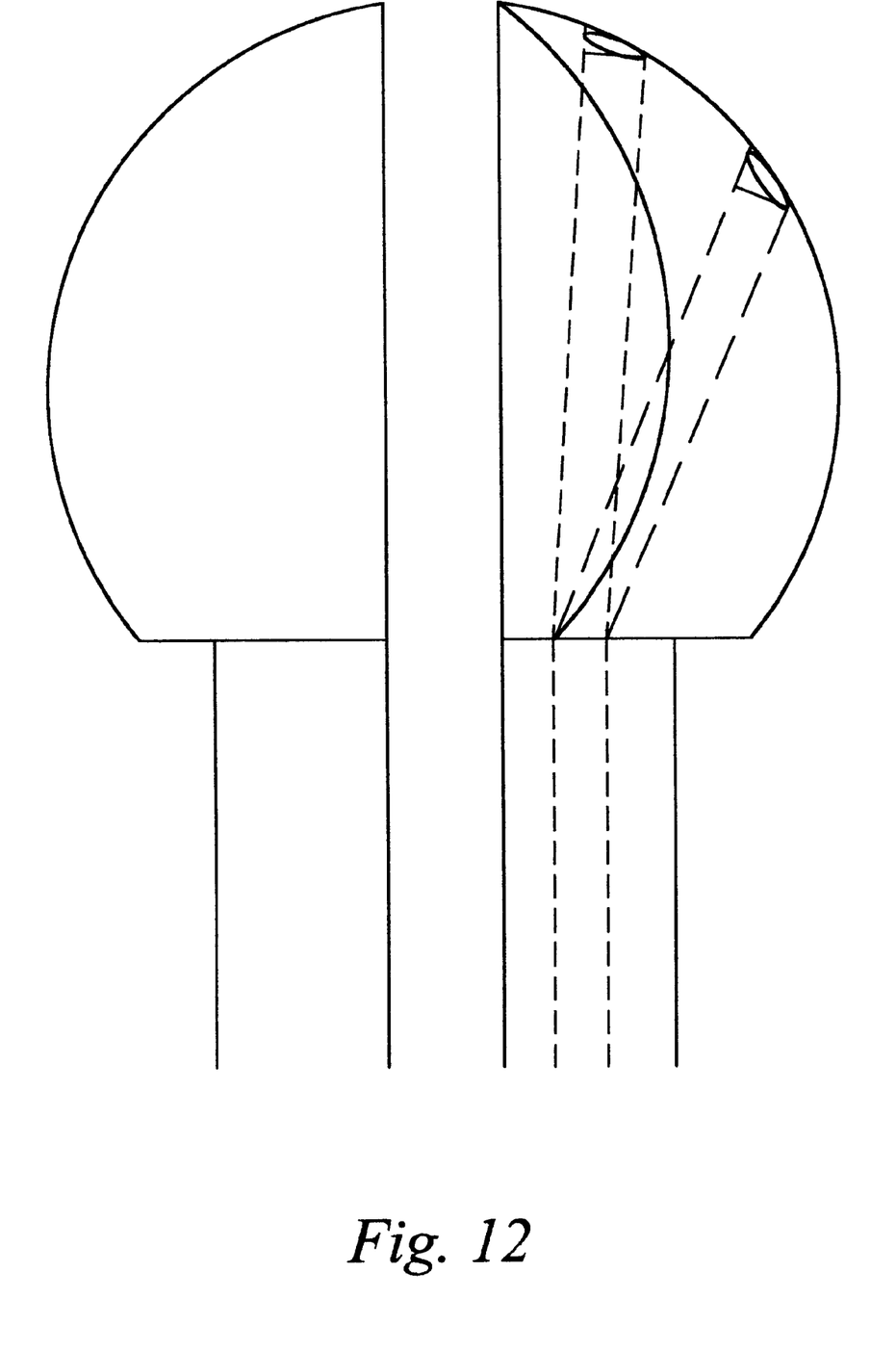

In order to enable the user to visualise location of the drill head ultrasound emitters may be located on or near the surface of the drill head. These would generally be directed forwardly such that the used is provided with an image of the tube as it extends away from the drilling site. Any suitable array of emitters may be used. One suitable array is illustrated in FIG. 11. It will be understood that each emitter will be connected to a suitable source via appropriate means which will extend through the drill head as illustrated for two emitter in FIG. 12.

Figure 13:
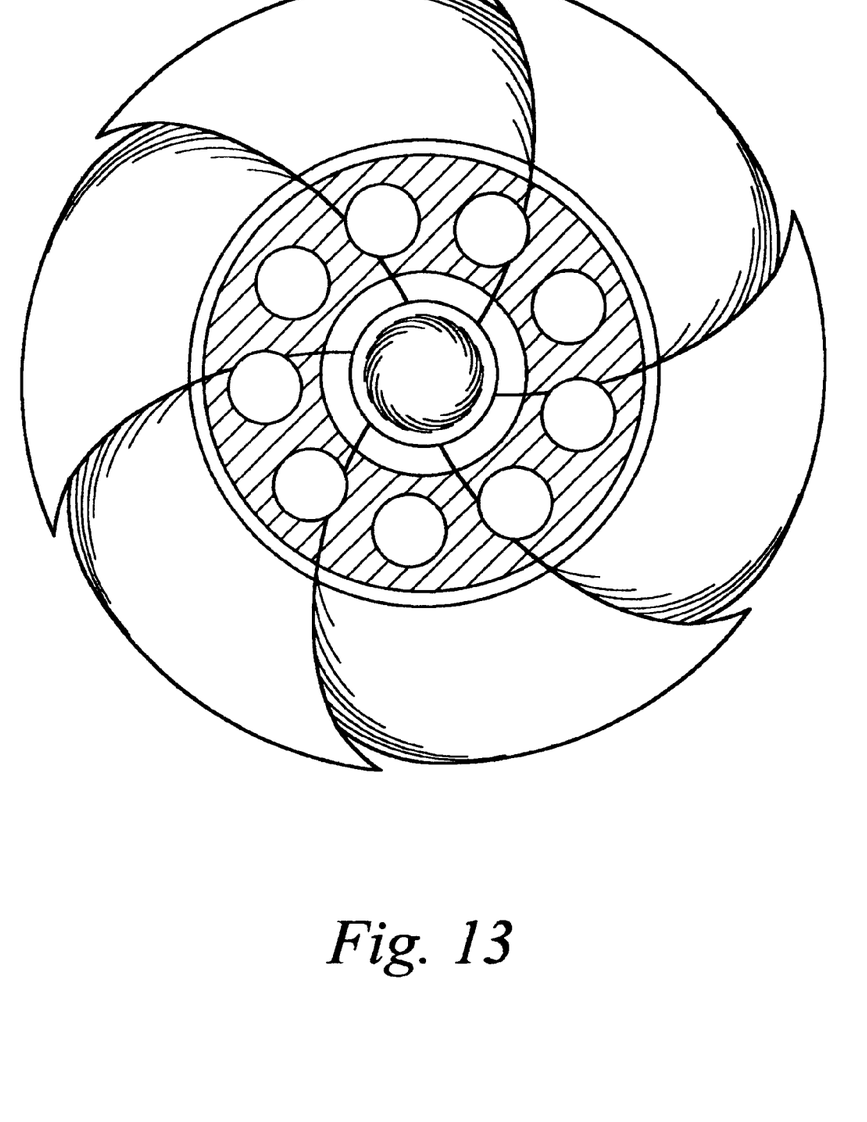

A number of conduits may extend through the centre of the shaft as illustrated in FIG. 13. These may be used to carry electrical leads, the reins, a suction line, a line for dispensing lubricant and any other requirement to access the drill head or the drilling site.

Figure 14:
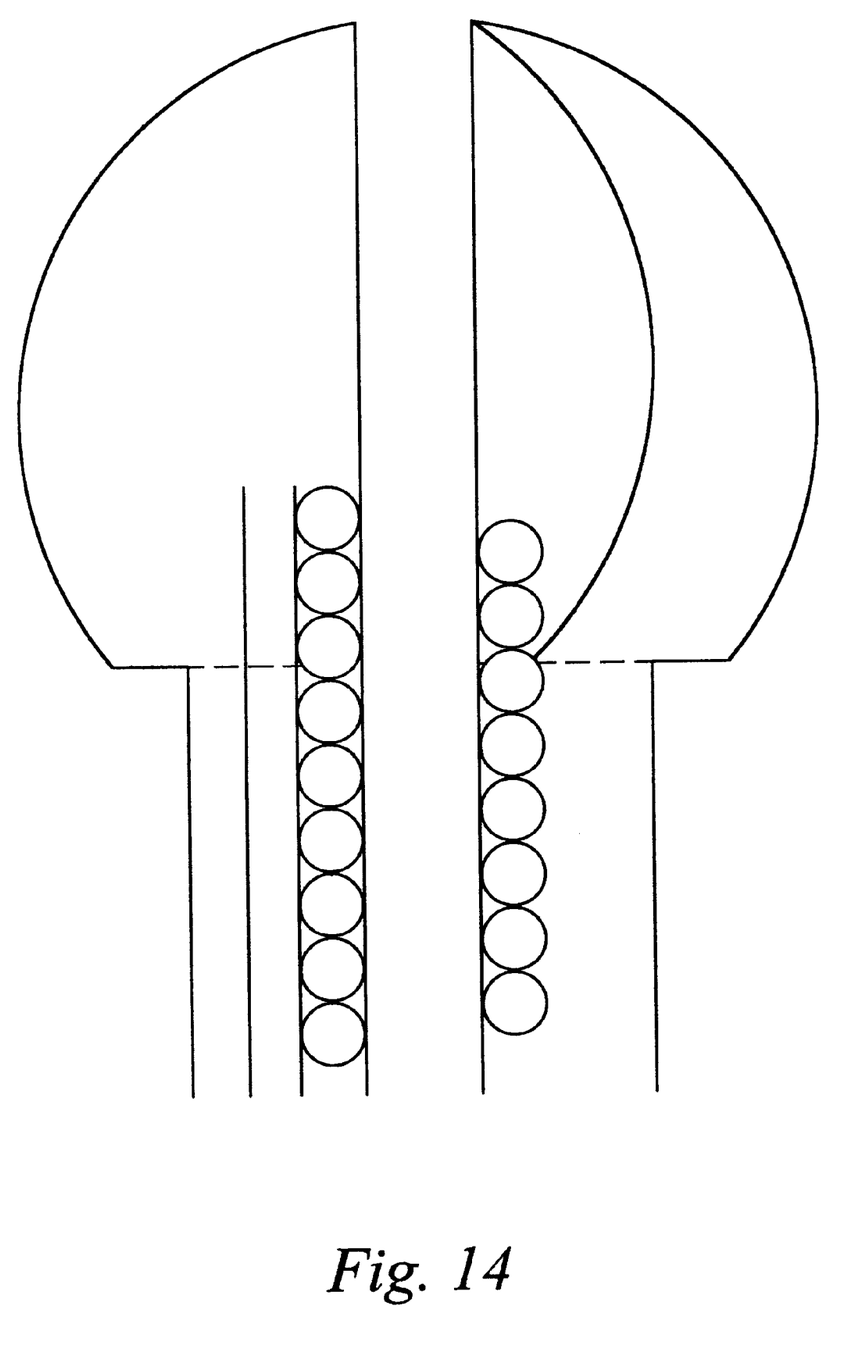

The drill head may be connected to the catheter by any suitable means but there is preferably a helical means to increase the flexibility between the drill head and the catheter. This is illustrated in FIG. 14.

Once the device has enabled a channel to be drilled to the occlusion, it may be removed and the now partial occlusion may be treated by conventional means. The anchoring means may be retained in the channel formed by the drill head to serve as the guide wire for the balloon catheter.

Whilst the device has been described particularly reference to the treatment of a total occlusion in a coronary artery, it will be understood that the same technique may be utilised to treat occlusions in other biological tubes and also in non-biological applications such as blocked tubes in domestic and industrial applications.

What is claimed is:

1. A drilling device comprising a catheter having a proximal and a distal end, a drill head located at the distal end of the catheter, the drill head having a tip, the drilling device further comprising a formation for anchoring the tip of the drill head against at least a portion of a face of occlusion while allowing a portion of the drill head to rotate, the drilling device further comprising at least one rein attached to the drill head to enable the direction of the drill head to be altered.

2. A drilling device according to claim 1, wherein the catheter is flexible.

3. A drilling device according to claim 1 or 2, wherein the anchoring formation is capable of being advanced by drilling.

4. A drilling device according to claim 3, wherein the anchoring formation comprises a drill tip, the drilling device further comprising a flexible drill wire attached to the drill tip.

5. A drilling device according to any one of claims 1 to 4 wherein the rotatable portion of the drill head is of hemispherical configuration.

6. A drilling device according to any one of claims 1 to 5, wherein the drilling device further comprises a detector for detecting one of electromagnetic radiation and ultrasound.

7. A drilling device according to claim 6, wherein the detector provides an image extending forwardly from the drill head.

8. A drilling device according to claim 6, further comprising a collar around the catheter, wherein the detector provides an image extending sidewardly from the collar around the catheter.

9. A drilling device according to claim 1 wherein the at least one reins is located in conduits running the length of the catheter.

10. A drilling device according to claims 1–6, 7, 8 and 9 further comprising a suction line.

11. A drilling device according to claims 1–6, 7, 8 and 9 further comprising a line for delivering a flushing liquid to the drill head.

12. A drilling device comprising a catheter having a distal end, a drill head located at the distal end of the catheter, means for anchoring the tip of the drill head against at least a portion of a face of occlusion while allowing the drill head to rotate, the drilling device further comprising ultrasound visualization means, and four reins enabling the direction of the drill head to be altered upwardly, downwardly, leftwardly or rightwardly.

13. A drilling device according to claim 1, further comprising an emitter for emitting one of the electromagnetic radiation and ultrasound.

14. A drilling device comprising a catheter having a proximal and a distal end and a drill head located a the distal end of the catheter, the drill head having a tip, the drilling device further comprising a formation for anchoring the tip of the drill head against at least a portion of a face of occlusion while allowing a cutting portion of the drill head to rotate, the drilling device further comprising a plurality of reins to enable the direction of the drill head to be altered.

* * * * *